(12) United States Patent
Souchay et al.

(10) Patent No.: US 9,770,215 B2
(45) Date of Patent: Sep. 26, 2017

(54) PROCESS AND DEVICE FOR DEPLOYING AN ANTI-SCATTERING GRID

(75) Inventors: Henri Souchay, Versailles (FR); Mathias Cisaruk, Paris (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 815 days.

(21) Appl. No.: 13/329,356

(22) Filed: Dec. 19, 2011

(65) Prior Publication Data

US 2012/0170711 A1    Jul. 5, 2012

(30) Foreign Application Priority Data

Dec. 29, 2010    (FR) ...................................... 10 61334

(51) Int. Cl.
*A61B 6/00* (2006.01)
*A61B 6/06* (2006.01)

(52) U.S. Cl.
CPC .............. *A61B 6/06* (2013.01); *A61B 6/4291* (2013.01); *A61B 6/502* (2013.01); *Y10T 29/49826* (2015.01)

(58) Field of Classification Search
CPC ............................... A61B 6/4291; A61B 6/502
See application file for complete search history.

(56) References Cited

U.S. PATENT DOCUMENTS

| 1,164,987 | A | * | 12/1915 | Bucky | .................... | B60C 27/16 |
| | | | | | | 152/191 |
| 3,684,885 | A | | 8/1972 | Cook | | |
| 6,181,773 | B1 | * | 1/2001 | Lee et al. | .................... | 378/155 |
| 6,304,632 | B1 | | 10/2001 | Rick et al. | | |
| 6,771,738 | B2 | | 8/2004 | Miotti et al. | | |
| 7,149,283 | B2 | | 12/2006 | Hoheisel | | |

(Continued)

FOREIGN PATENT DOCUMENTS

| EP | 0994489 A1 | 4/2000 |
| FR | 2939019 A1 | 6/2010 |
| WO | 2010092615 A1 | 8/2010 |

OTHER PUBLICATIONS

Unofficial translation of French Search Report and Written Opinion issued in connection with corresponding FR Application No. 1061334 dated Aug. 26, 2011.

*Primary Examiner* — Dani Fox
(74) *Attorney, Agent, or Firm* — GE Global Patent Operations; Marc A. Vivenzio

(57) ABSTRACT

A process for deploying an anti-scattering grid in a mammograph is provided. The mammograph comprises a radiation source configured to emit radiation for taking mammographic images of a patient, a radiation detector comprising a network of sensors arranged periodically with a first pitch, and an anti-scattering grid arranged between the source and the detector, the anti-scattering grid comprising absorption laminates of radiations arranged parallel to each other and distributed periodically with a second pitch. The process comprises: displacing the anti-scattering grid relative to the detector or displacing the detector relative to the anti-scattering grid during emission of radiation; and adapting the second pitch to the first pitch, wherein displacement is perpendicular to the direction of the laminates of the anti-scattering grid, the laminates being arranged parallel to a side of the anti-scattering grid positioned against the patient.

19 Claims, 3 Drawing Sheets

(56) References Cited

U.S. PATENT DOCUMENTS

| | | |
|---|---|---|
| 7,474,735 B2 | 1/2009 | Spahn |
| 2002/0101960 A1 | 8/2002 | Nokita |
| 2004/0007671 A1* | 1/2004 | Sipila .................... G01T 1/2018 250/370.01 |
| 2008/0080673 A1 | 4/2008 | Yamakita |
| 2009/0003519 A1* | 1/2009 | Defreitas et al. ............... 378/37 |
| 2011/0069816 A1* | 3/2011 | Shaw et al. ................... 378/154 |
| 2011/0274252 A1 | 11/2011 | Kuwaabara |

* cited by examiner

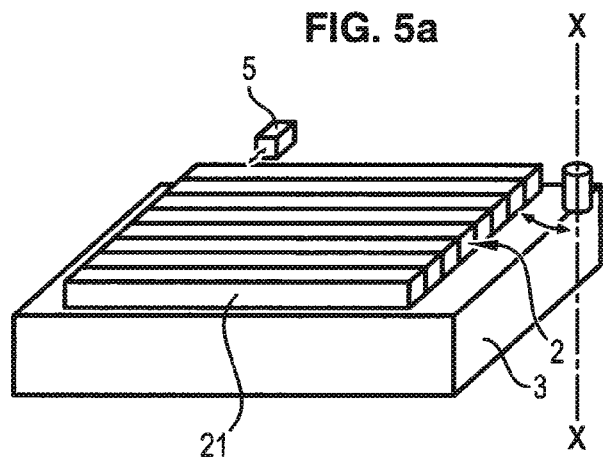
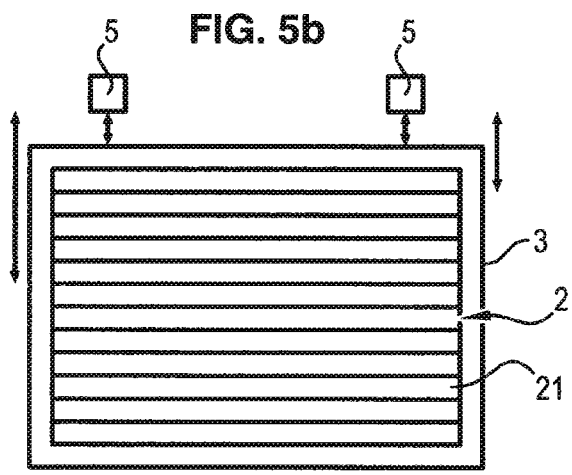
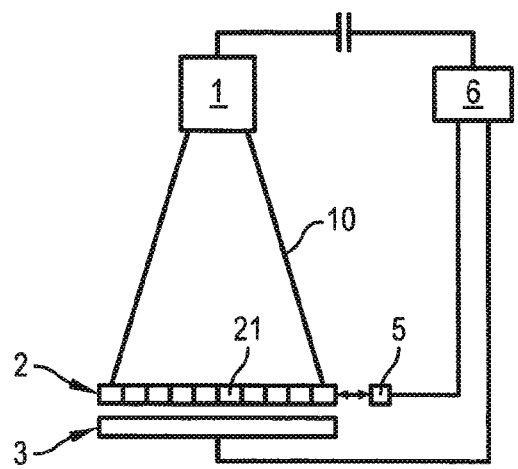

PROCESS AND DEVICE FOR DEPLOYING AN ANTI-SCATTERING GRID

BACKGROUND OF THE INVENTION

Field of the Invention

The present disclosure is generally related to the field of medical imaging, and more particularly the field of radiography. Embodiments of the present invention relate to the field of the deploying anti-scattering grids used to improve radiographic frames by filtering the photons scattered by the organ under study, and keeping only the photons emitted by the source. Embodiments of the present invention can be utilised within the scope of mammography, and more particularly within the scope of mammary tomosynthesis, which takes a series of frames at different angles to produce a 3D image of the object being studied.

Description of the Prior Art

Anti-scattering grids are used widely in radiography devices to eliminate effects due to parasite scattering of some photons, taking place in the organ studied in said devices. These grids filter photons scattered by the organ being studied and mainly keep only photons actually originating from the radiation source of the radiography device, thus improving the contrast on the images obtained.

In reference to FIG. 1, a conventional use of an anti-scattering grid 2 is illustrated. This grid 2 is placed between an organ of a patient P to be studied and who is irradiated by a radiation source 1, and a radiation detector 3 comprising a network of sensors 31 (illustrated in FIG. 3) distributed periodically with a period $p_d$ (later called the pitch of the detector).

The assembly made up of the grid and the detector is positioned according to a plane perpendicular to the plane $P_T$ of the torso of the patient. By way of non-limiting example, illustrated in FIG. 1, the patient P can be standing and the grid and the detector are then on a horizontal plane, the walls of the grid and of the detector in contact with the patient being tangential to the plane $P_T$.

The grid 2 is generally constituted by alternating radio-opaque and radio-transparent laminates 21, the laminates 21 being parallel and distributed periodically, with a pitch $p_g$ between two radio-opaque laminates so that the scattered photons are absorbed by the radio-opaque laminates and the photons coming directly from the source 1 are transmitted to the detector 3 of the radiography device.

One drawback of using such a grid is that an image of the grid appears on the detector. Also, alternating laminates can cause interference figures, or moiré effect, on the detector and deteriorate the quality and legibility of the frame obtained.

For deleting the image of the grid, a solution known in mammography and schematically illustrated in FIGS. 1 and 2a is used, consisting of animating the grid 2 by vibration movement perpendicular to the direction according to which the laminates 21 extend, that is, parallel to the side of the grid against which the patient can be positioned.

In terms of mammary tomosynthesis, acquiring a 3D image of the object means acquiring a series of images of the object according to different relative angular positions between the source and the detector. For this to occur, the radiation source 1 is pivoted about an axis Y-Y, illustrated in FIG. 2b, perpendicular to the plane of the torso of the patient P, since pivoting of the source according to an axis parallel to the plane of the torso $P_T$ of the patient P would create risk of irradiating the latter.

This configuration necessarily causes the grid to pivot by 90° in its plane so that the trajectory of the source 1 remains near the focal line of the grid 2.

For reasons associated with bulk, as illustrated in FIG. 3, it then becomes difficult to execute displacement of the grid 2 perpendicularly to the direction of the laminates.

In effect, in reference to FIG. 3, the detector 3 and the anti-scattering grid 2 are located under a cap 4 likewise supporting the breast of the patient throughout examination. Legislation imposes that the distance between the costal grid of the patient and the closest sensors 31 of the detector 3 be less than 5 mm.

This interval must also comprise the thickness of the cap 4 and the edge of the grid 2 which is not constituted by laminates. Given these elements, the space remaining for the grid 2 to move is less than 2 mm.

Since the movement required to erase the image of the grid is of the order of 10 mm, it cannot occur according to an axis perpendicular to the plane of the torso $P_T$ of the patient.

There is therefore a need for a novel technique for making an image with a grid having laminates parallel to the chest of the patient P, while at the same time avoiding the image of the grid and the moiré effects on the detector.

Solutions adopted in mammary tomosynthesis in the prior art to eliminate the image of the grid on the detector propose adapting the pitch of the grid $p_g$ to the pitch of the detector $p_d$, so that the pitch of the grid $p_g$ is for example equal to a multiple of the pitch $p_d$ of the detector.

Another solution presented in document FR 2,939,019 consists of adapting the pitch of the grid to the Nyquist frequency of the detector then digitally filtering the image of the grid on the detector.

But, none of these solutions gives a completely satisfactory result. In particular, even if the grid is no longer visible on the frame, a moiré effect remains, linked to interferences between the laminates of the grid and the network of sensors of the detector.

BRIEF SUMMARY OF THE INVENTION

Embodiments of the present invention provide a process and device for deploying an anti-scattering grid, applicable to mammography and to mammary tomosynthesis, which eliminates both the image of the grid on the detector and the residual moiré effects.

According to one embodiment of the present invention, a process for deploying an anti-scattering grid in a mammograph is provided. The mammograph comprises a radiation source configured to emit radiation for taking mammographic images of a patient, a radiation detector comprising a network of sensors arranged periodically with a first pitch, and an anti-scattering grid arranged between the source and the detector, the anti-scattering grid comprising absorption laminates of radiations arranged parallel to each other and distributed periodically with a second pitch. The process comprises: displacing the anti-scattering grid relative to the detector or displacing the detector relative to the anti-scattering grid during emission of radiation; and adapting the second pitch to the first pitch, wherein displacement is perpendicular to the direction of the laminates of the anti-scattering grid, the laminates being arranged parallel to a side of the anti-scattering grid positioned against the patient.

According to another embodiment of the present invention, a mammograph is provided. The mammograph comprises a radiation source configured to emit radiation for taking mammographic images of a patient. The mammograph further comprises a radiation detector comprising a network of sensors arranged periodically with a first pitch and an anti-scattering grid arranged between the source and the detector, the anti-scattering grid comprising absorption laminates of radiations arranged parallel to each other and distributed periodically with a second pitch. The mammograph comprises at least one actuator configured to displace the anti-scattering grid relative to the detector or displace the detector relative to the anti-scattering grid during emission of radiation, wherein displacement is perpendicular to the direction of the laminates of the anti-scattering grid, the laminates being arranged parallel to a side of the anti-scattering grid positioned against the patient, and wherein the second pitch is adapted to the first pitch during displacement.

BRIEF DESCRIPTION OF THE DRAWINGS

Other characteristics, aims and advantages of the present invention will emerge from the following detailed description, with respect to the attached figures given by way of non-limiting examples and in which:

FIG. 5a illustrates an example for deploying relative movement according to an embodiment of the present invention;

FIG. 5b illustrates, in plan view, an example for deploying relative movement according to an embodiment of the present invention; and FIG. 6 schematically illustrates a mammograph according to an embodiment of the present invention.

DETAILED DESCRIPTION OF THE INVENTION

Figure 1:
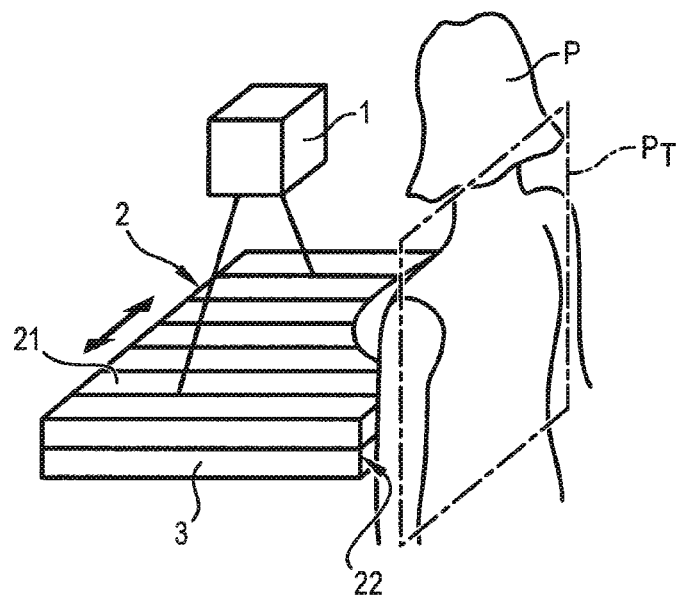
FIG. 1 illustrates a process for deploying an anti-scattering grid according to the prior art.
Figure 2A:
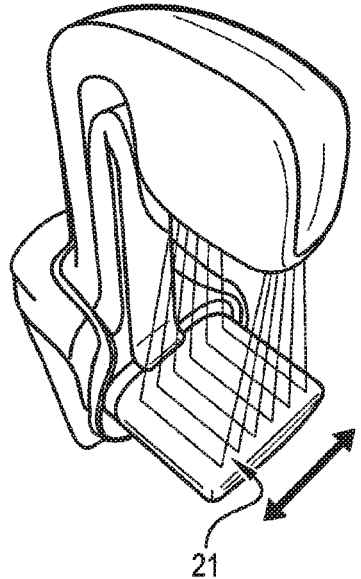
FIG. 2a illustrates a traditional mammography device using an anti-scattering grid.
Figure 2B:
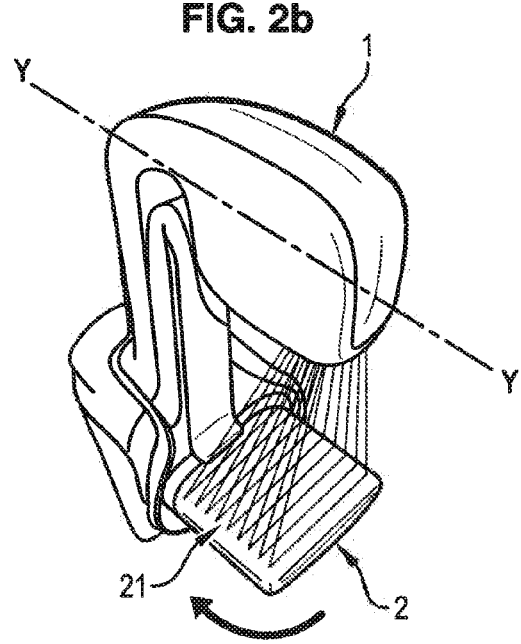
FIG. 2b illustrates a tomosynthesis device deploying an anti-scattering grid.
Figure 3:
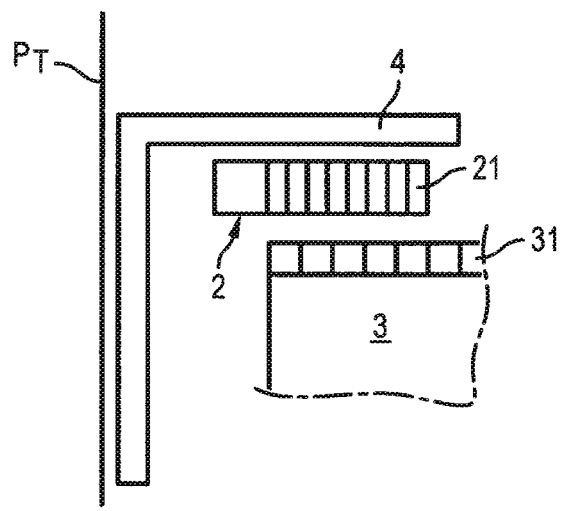
FIG. 3 illustrates a configuration of an anti-scattering grid on a radiation detector.
Figure 4:
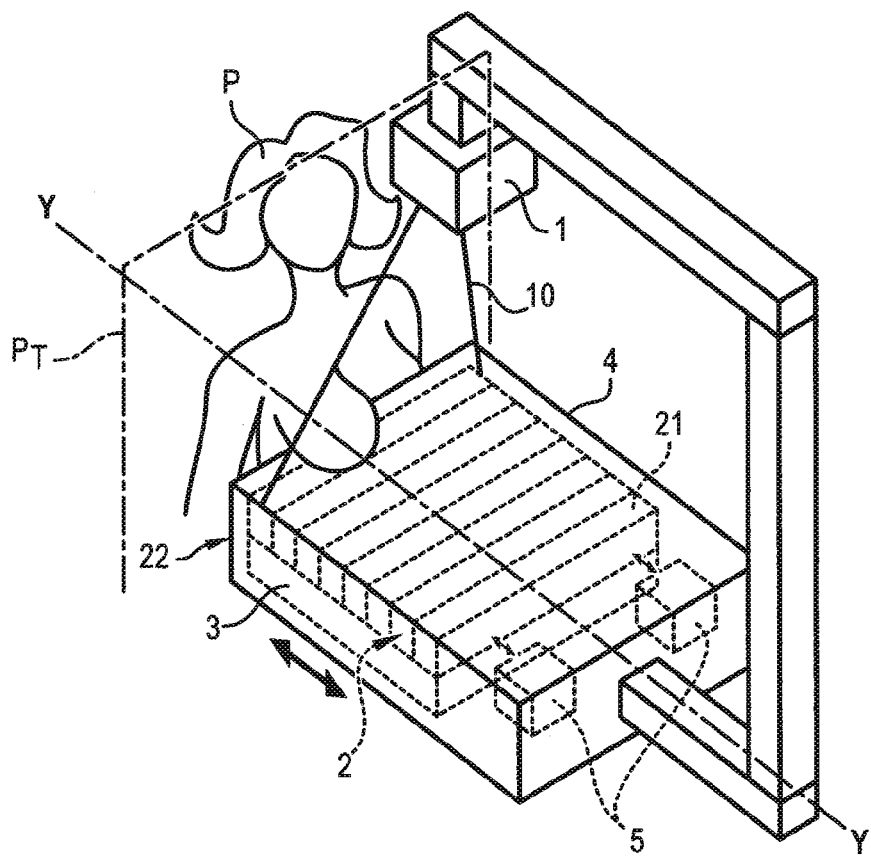
FIG. 4 schematically illustrates execution of a mammograph according to an embodiment of the present invention.

In reference to FIG. 4, a mammograph is illustrated comprising a radiation source 1, for example of X-ray type, emitting radiation 10 designed to illuminate the breast of a patient P of whom images are to be taken during a pause time T. The radiations transmitted then reach a detector 3 made up of a network of sensors 31 distributed periodically with a pitch $p_d$ of the detector, of the order of 100 to 200 μm.

An anti-scattering grid 2 is interposed between the source 1 and the detector 3, more precisely between the breast of the patient P and the detector 3, so as to stop radiations scattered by the breast of the patient P not coming directly from the source 1.

This anti-scattering grid 2 is placed immediately above the detector 3, and is held by means of a cap 4. This cap also forms the support of the breast of the patient to be examined.

The grid 2 comprises alternating radio-opaque laminates 21, for example constituted by metal, and radio-transparent laminates 21 which can be cavities of the grid, the laminates 21 being parallel and distributed periodically with a pitch $p_g$ between two radio-opaque laminates, This pitch $p_g$ is for example adapted to that of the detector, that is, it can be a multiple of the pitch $p_d$ of the detector 3, for example equal to the pitch $p_d$ of the detector 3, or even be a multiple of the Nyquist frequency of the detector 3. For example, a pitch of the grid $p_g$ may be about 100 μm. The grid 2 may have a thickness of the order of about 1 mm, and sides of a length of the order of about 24×30 cm.

The laminates 21 of the grid are oriented according to a direction parallel to one side 22 of the grid 2 against which the patient P can be positioned. As such, the source 1 is capable of pivoting about an axis Y-Y, thus enabling 3D images to be taken.

The mammograph also comprises one or more actuators 5, whereof two are illustrated by way of non-limiting example in FIG. 4. This actuator or these actuators 5 permit relative movement between the grid 2 and the detector 3 explained hereinbelow, by shifting the grid 2 relative to the detector 3 or alternatively by shifting the detector 3 relative to the grid 2, over a time T corresponding at least to the exposure time of the patient P.

The actuator or the actuators 5 can be located on the same side of the grid 2, and located under, as it is, under the cap 4 which holds the grid and the detector.

Given the abovementioned spread of less than 2 mm between the edge of the grid 2 and the side of the cap 4 against which the patient P can be positioned, the actuator or the actuators 5 can be located to the side opposite this side of the cap 4—this side also corresponding to the side 22 of the grid 2 against which the patient P can be positioned. This also reduces the added bulk caused by addition of this actuator or these actuators 5.

Finally, in reference to FIG. 6, the source 1, the actuator or the actuators 5 and the detector 3 are connected to a control and processing unit 6 which both manages the source 1 and the actuator or the actuators 5 and also ensures acquisition and processing of images, if needed.

Relative movement between the grid 2 and the detector 3 eliminates the moiré on the detector 3 by varying the phase of the latter during the exposure time T. For this, it comprises at least one component according to a direction perpendicular to the direction in which the laminates 21 of the grid 2 extend. In addition, the amplitude of the movement of the grid 2 or of the detector 3 according to this component, irrespective of its nature, should be at least one grid pitch $p_g$ in every sensor 31 of the detector 3 throughout exposure time T.

According to a first embodiment of relative displacement between the grid 2 and the detector 3, the actuator or the actuators 5 can be piezoelectric motors. In this case, they shift the grid 2 or the detector 3 according to a translation movement along an axis perpendicular to the direction of the laminates 21, that is, perpendicularly to the side 22 of the grid 2 against which the patient P can be positioned.

In a variant illustrated in FIG. 5a, the mammograph comprises just one motor 5 connected to a reducer and a cam for executing angular displacement, in its plane, of the grid 2 or of the detector 3 about an axis X-X illustrated in the figure, by means of rotation whereof the centre is located outside the grid 2, respectively the detector 3. This variant has the advantage of using just one motor, reducing usage costs of such a mammograph.

In this case, the amplitude of rotation corresponding to the amplitude of displacement is adapted as a function of the distance between the grid 2 (or the detector 3), and the centre of rotation. This embodiment modifies the moiré phase non-uniformly during the exposure time T, another way of deleting the moiré figures.

As per another variant illustrated in FIG. 5b, the mammograph comprises at least two motors 5, actuating the grid 2 respectively the detector 3—at different speeds and preferably non-multiple integers such that they are desynchronised, which also modifies the moiré phase non-uniformly during the exposure time T.

The movement of the grid 2—respectively of the detector 3—whereof especially some components such as its displacement speed and its amplitude, is dependent of the exposure time or pause time T. This movement can for example be done at constant speed.

The total amplitude of the movement of the grid 2—respectively of the detector 3—can thus be equal to k times the pitch of the grid $p_g$, k being an integer or a semi-integer between 1 and 50, depending on the pitch $p_g$ of the grid.

In the case of a grid pitch equal to 100 microns, k can be between 1 and 20 inclusive, corresponding to displacement of the grid 2—respectively of the detector 3—by amplitude between around 100 μm and 2 mm.

This displacement of minimal amplitude can be done in the abovementioned small space (of the order of 2 mm) between the cap 4 and the grid 2.

This movement, in conjunction with adaptation of the pitch of the grid $p_g$ to the pitch of the detector $p_d$, eliminates the image of the grid on the detector, as well as the residual moiré effects. Movement of only the grid 2—respectively of the detector 3—by likewise minimal amplitude would not eliminate the image of the grid 2.

The speed v of the grid 2—respectively of the detector 3—enabling this displacement during the exposure time T can be constant and equal to v=Δx/T where Δx is the total amplitude of the displacement of the grid.

Alternatively, the grid 2—or the detector 3, if required—can be animated by oscillatory movement which can be periodical or not.

In the case of periodical movement, the speed v of the grid 2—respectively of the detector 3—can be constant throughout each half period.

The amplitude of the movement of the grid 2—respectively of the detector 3—on oscillation can be equal to k times the pitch of the grid, k being an integer or a semi-integer between 1 and 50, depending on the pitch $p_g$ of the grid.

In the case of a grid pitch equal to 100 microns, k can be between 1 and 20 inclusive, corresponding to displacement of the grid 2 by amplitude between around 100 μm and 2 mm.

Because of this mammograph and the process for deploying the grid which is executed, neither the image of the grid on the detector nor any moiré effect appears on the images obtained.

The invention claimed is:

1. A process for deploying an anti-scattering grid in a mammograph comprising a radiation source configured to emit radiation for taking mammographic images of a patient, a radiation detector comprising a network of sensors arranged periodically with a first pitch, and an anti-scattering grid arranged between the source and the detector, the anti-scattering grid comprising radiation adsorbing laminates arranged parallel to each other and distributed periodically with a second pitch, the process comprising:
    displacing the anti-scattering grid or the detector during radiation emission,
    adjusting the second pitch in relation to a setting of the first pitch and;
    wherein displacement is rotational, during radiation emission, around an axis perpendicular to a plane of the anti-scattering grid, or perpendicular to a plane of the detector, wherein the axis defines a center of rotation located outside the anti-scattering grid.

2. The process as claimed in claim 1, wherein displacement has minimal amplitude of the second pitch.

3. The process as claimed in claim 1, wherein displacing comprises shifting the anti-scattering grid or the detector in at least two points with speeds different to each other.

4. The process as claimed in claim 1, wherein the anti-scattering grid or the detector is displaced at constant speed.

5. The process as claimed in claim 4, wherein the amplitude of displacement of the anti-scattering grid, or of the detector, is equal to k times the second pitch, wherein k is an integer or a semi-integer.

6. The process as claimed in claim 5, wherein k is between about one and about twenty.

7. The process as claimed in claim 1, wherein displacement is oscillatory.

8. The process as claimed in claim 7, wherein displacement is periodical.

9. The process of claim 1, further comprising moving the source relative to the detector to acquire three-dimensional mammographic images.

10. The process as claimed in claim 1, wherein an amplitude of the rotation around the axis is a function of a distance between the anti-scattering grid or the detector and the center of rotation.

11. A mammograph comprising:
    a radiation source configured to emit radiation for taking mammographic images of a patient;
    a radiation detector comprising a network of sensors arranged periodically with a first pitch;
    an anti-scattering grid arranged between the source and the detector, the anti-scattering grid comprising radiation adsorbing laminates arranged parallel to each other and distributed periodically with a second pitch; and
    an actuator configured to displace the detector or the scattering grid relative to each other during emission of radiation;
    an axis perpendicular to a plane of the anti-scattering grid or a plane of the detector;
    a center of rotation defined by the axis located outside the anti-scattering grid;
    wherein displacement is rotational, during radiation emission, around the axis perpendicular to the plane of the anti-scattering grid or perpendicular to the plane of the detector, and wherein the second pitch is adjusted in relation to a setting of the first pitch during displacement.

12. The mammograph as claimed in claim 11, wherein the actuator is configured to displace the anti-scattering grid or the detector at constant speed.

13. The mammograph as claimed in claim 11, wherein the actuator comprises a piezoelectric motor.

14. The mammograph as claimed in claim 11, wherein the actuator comprises a motor connected to a reducer and a cam.

15. The mammograph as claimed in claim 11, wherein the actuator is arranged on a side of the anti-scattering grid opposite the side of the grid positioned against the patient.

16. The mammograph as claimed in claim 11, wherein the second pitch is a multiple of the first pitch.

17. The mammograph as claimed in claim 11, wherein the second pitch is a multiple of the Nyquist frequency of the detector.

18. The mammograph as claimed in claim 11, further comprising a control and processing unit configured to control the source and the detector and configured to control acquisition and processing of images.

19. The mammograph as claimed in claim 11, wherein an amplitude of the rotation around the axis is a function of a distance between the anti-scattering grid or the detector and the center of rotation.

* * * * *